US00PP31185P2

(12) United States Plant Patent
Hansen

(10) Patent No.: US PP31,185 P2
(45) Date of Patent: Dec. 3, 2019

(54) ***KNIPHOFIA* PLANT NAMED 'HOT AND COLD'**

(50) Latin Name: *Kniphofia hybrida*
Varietal Denomination: Hot and Cold

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,346

(22) Filed: Nov. 5, 2018

(51) Int. Cl.
*A01H 6/00* (2018.01)
*A01H 5/02* (2018.01)

(52) U.S. Cl.
USPC ..... Plt./443

(58) Field of Classification Search
USPC ..... Plt./443
CPC ..... A01H 6/00; A01H 5/02
See application file for complete search history.

*Primary Examiner* — Keith O. Robinson

(57) ABSTRACT

A new and distinct cultivar of Red Hot Poker plant named *Kniphofia* 'Hot and Cold' with long, gracefully-arching, strap-like, keeled, glaucous, gray-green foliage and numerous scapes beginning in late spring and repeating for six weeks. Habit is densely growing, winter-hardy, tolerant of lodging, heat, deer and rabbits. Numerous scapes of vivid reddish buds and contrasting open flowers of pale greenish-yellow on tall scapes beginning in late spring and repeating repeating for six weeks. The new plant is useful for landscaping as a specimen, en masse, or as a long-lasting cut flower.

1 Drawing Sheet

Botanical classification: *Kniphofia hybrida.*
Variety denomination: 'Hot and Cold'.

BACKGROUND AND ORIGIN OF THE PLANT

The present invention relates to the new and distinct Red Hot Poker, *Kniphofia* 'Hot and Cold' hybridized under the direction of the inventor at a wholesale perennial nursery in Zeeland, Mich., USA on Aug. 16, 2012 and seeds were collected in the fall of 2012. The new plant was a single seedling selection resulting from a cross of 'Echo Mango' U.S. Plant Pat. No. 21,706 as the female parent or seed parent and 'Sally's Comet' (not patented) as the male parent or pollen parent. The plant passed initial evaluation in the summer of 2014 and was subsequently given the breeder code 12-3-1 prior to naming. *Kniphofia* 'Hot and Cold' has been successfully asexually propagated by division method since 2014 at the same wholesale perennial nursery in Zeeland, Mich. and subsequently by shoot tip tissue culture, and both methods have been found to be stable and produce identical plants that maintain the unique characteristics of the original plant through multiple generations.

No plants of *Kniphofia* 'Hot and Cold' have been sold, in this country or anywhere in the world, with this name or any other name, prior to the filing of this application, nor has any disclosure of the new plant been made prior to the filing of this application except that which was disclosed within one year of the filing of this application and was either derived directly or indirectly from the inventor.

SUMMARY OF THE PLANT

*Kniphofia* 'Hot and Cold' differs from its parents as well as all other *Kniphofia* known to the applicant. The most similar known *Kniphofia* cultivars are: the female parent 'Echo Mango' which has lighter orange buds with less reddish hue with flowers opening more light yellow on slightly taller scapes. The male parent 'Sally's Comet' has yellowish buds and open flowers with no orange hue on taller scapes. The new plant has greater contrast in flower bud and open flower color than 'Redhot Popsicle' U.S. Plant Pat. No. 24,036, 'Fire Glow' U.S. Plant Pat. No. 22,894 and 'Red Rocket' U.S. Plant Pat. No. 21,905. The new plant is taller in flower scape than 'Orange Vanilla Popsicle' U.S. Plant Pat. No. 24,292 and shorter in scape than 'Echo Duo' U.S. Plant Pat. No. 24,508.

*Kniphofia* 'Hot and Cold' differs from these above cultivars and all cultivars known to the inventor in that it has:

1. Gracefully arching, strap-like, keeled, gray-green foliage.
2. Rapidly growing, dense habit, winter-hardy, heat tolerant, rabbit and deer tolerant, large-sized clumps.
3. Numerous spikes of vivid red flower buds contrasting with pale greenish-yellow open flowers on moderately tall stems;
4. Flowering beginning the last week of spring and continuing for about six weeks in Michigan.

BRIEF DESCRIPTION OF THE DRAWINGS

The photographs of *Kniphofia* 'Hot and Cold' demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
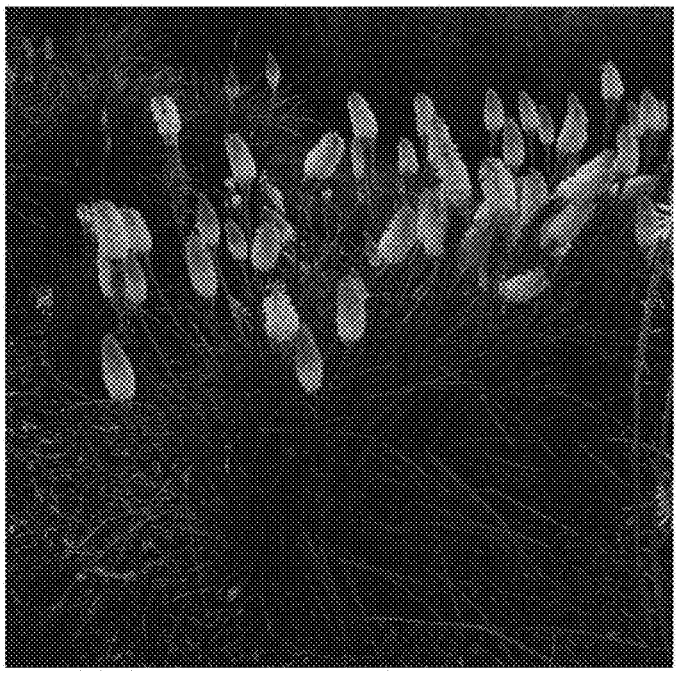
FIG. 1 shows the side-view habit of a five-year-old plant in midseason flowering.
Figure 2:
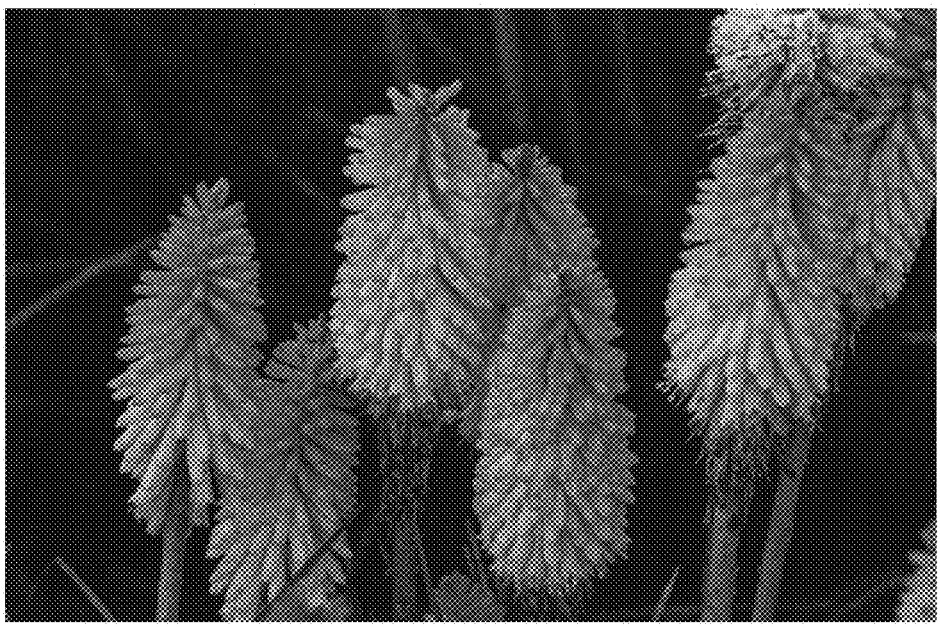
FIG. 2 shows a close-up of the flowers and buds.

The following descriptions and color references are based on the 2015 edition of The Royal Horticultural Society Colour Chart except where common dictionary terms are used. The new plant, *Kniphofia* 'Hot and Cold', has not been observed under all possible environments. The phenotype may vary slightly with different environmental conditions, such as temperature, light, fertility, moisture and maturity levels, but without any change in the genotype. The following observations and size descriptions are of a five-year-old plant in a trial garden of a wholesale perennial nursery in Zeeland, Mich. under full sun with supplemental water and fertilizer as needed.

Botanical classification: *Kniphofia* hybrid;

Parentage: *Kniphofia* 'Echo Mango' as the female or seed parent and 'Sally's Comet' as the male or pollen parent;

Propagation method: By garden division of the crown and shoot tip tissue culture;

Growth rate: Vigorous, flowering in 3.5 liter containers in about 10 to 12 weeks from a 25 mm plug liner in late winter to spring and from a one-year-old bare root plant to flowering in 6 to 8 weeks in a 4.0 liter container;

Rooting habit: Fibrous from base of crown, lightly branching; color nearest RHS 158C;

Plant description: Dense, rhizomatous, acaulescent, perennial clump with long thin foliage to about 145.0 cm across and about 83.0 cm tall; flowering to about 85.0 cm tall; about 72 peduncles per plant;

Leaves: Linear; keeled at base, triangular in distal half; arranged about 8 leaves per basal division; apex narrowly acute; base sessile, truncate, clasping; margin entire, micro-dentate to fimbrillate; abaxial midrib micro-dentate; no fragrance observed;

Leaf size: To about 85.0 cm long and 17.0 mm across at base, average about 75.0 cm long and 15.0 mm across at base;

Leaf color: Young base nearest RHS 150D both abaxial and adaxial, distally between RHS 144A and RHS 138A both abaxial and adaxial; mature both surfaces nearest RHS 146B;

Leaf venation: Parallel; color between RHS 146B and RHS 146A;

Stem: Acaulescent; crown about 20.0 mm across at base;

Inflorescence: In spike-like raceme; cylindrical; about 170 flowers per stem; flowering portion to about 28.0 cm tall and about 6.0 cm across; lasting about three weeks; flower spacing less than 1.0 mm apart on raceme in distal region and about 2.5 cm in lowest flowers;

Peduncle: Cylindrical, solid not fistulose; glabrous; slightly glaucous; erect to about 85.0 cm long and 10.0 mm diameter; average 76.0 cm tall and 9.0 mm diameter;

Peduncle color: Nearest RHS 144A;

Buds one day prior to opening: Ellipsoidal to tubular with slightly swollen subacute apex and rounded base; glabrous; lustrous; about 19.0 mm long and about 3.0 mm diameter at base and 4.5 mm diameter at widest point near apex; five days prior to anthesis about 14 mm long and 3.3 mm across;

Bud attitude: Beginning outwardly and drooping as maturing toward anthesis;

Bud color: Abaxial distal and dorsal portions nearest RHS 23D, tepal midrib nearest RHS 23A; five days prior to anthesis distally nearest RHS 24A, proximally nearest RHS 45A with veins nearest RHS N30B;

Flowers: Fistulose, forming tubular corolla; perfect; actinomorphic; individually open and effective about three to four days; about 24.0 mm long and about 4.5 mm diameter at base;

Corolla size: To about 21.0 mm long, fused in basal about 19.0 mm; face to about 8.0 mm tall and about 8.0 mm wide; fused tube about 4.5 mm diameter near base and about 5.5 mm near throat;

Flower attitude: Drooping;

Flower fragrance: None detected;

Flowering period: Individual racemes effective for about 3 weeks; beginning late spring in Michigan for about six week;

Tepals: Six, in two sets of three; both sets with acute apices and fused in basal 19.0 mm forming tube; margin entire; glabrous and lustrous abaxial and adaxial; about 21.0 mm long and about 5.5 mm across just above fusion point;

Tepal color mature abaxial: Both inner and outer sets identically nearest RHS 10D; adaxial midribs between RHS 3B and RHS 2B;

Androecium: Six; variable lengths;

*Filaments*.—Six; exserted; cylindrical; glabrous; lustrous; from about 17.0 to 24.0 mm long and about 0.5 mm diameter; color nearest RHS 8D.

*Anther*.—Dorsifixed; longitudinal, ellipsoidal; about 2.0 mm long and 1.5 mm across and 1.0 mm across; color nearest RHS 13A.

*Pollen*.—Abundant: color nearest RHS 11A.

Gynoecium: Single; about 22.0 mm long; slightly exserted;

*Style*.—Terete; glabrous; lustrous; about 20.0 mm long and 0.3 mm diameter: color nearest RHS 2D at base, nearest RHS 24D in proximal 4 mm and nearest RHS 24A in distal 1.0 mm.

*Stigma*.—Flattened, round; about 0.3 mm across; color nearest RHS 19A.

*Ovary*.—Superior; globose; rounded apex, truncate base; about 2.5 mm long and 2.5 mm diameter; color nearest RHS 144C.

Pedicel: Cylindrical; glabrous; stiff; drooping; about 2.0 mm long and about 0.7 mm diameter;

Pedicel color: Five days prior anthesis nearest RHS N34A, one day prior anthesis nearest RHS 173A, and four days after anthesis nearest RHS 146C;

Bracts: Lanceolate; papery and translucent; at cauline nodes and subtending individual flowers; with acute apices and truncate base; to about 11.0 mm long and 5.0 mm across at base; decreasing distally; average about 5.0 mm long and 2.0 mm across; color blushed with nearest RHS 161D;

Fruit: Tri-valved loculicidal capsule; ellipsoidal; about 6.0 mm long and 5.0 mm across; glabrous; with rounded to slightly acute apex and rounded base; typically six to twelve seeded; color upon maturity nearest RHS 200A;

Seed: Irregular with angular sides, acute apex and base; about 3.5 mm long and 2.5 mm across; color nearest RHS 200A;

Disease and pest resistance: 'Hot and Cold' resistance beyond that of other *Kniphofia* has not been observed. The plant grows best with good drainage and is able to tolerate some heat when established. Hardiness at least from USDA zone 6 through 9 and 5b with protection.

I claim:

1. A new and distinct cultivar of Red Hot Poker plant named *Kniphofia* 'Hot and Cold' as herein described and illustrated.

* * * * *